(12) United States Patent
Watanabe et al.

(10) Patent No.: US 9,715,021 B2
(45) Date of Patent: Jul. 25, 2017

(54) RADIATION IMAGING APPARATUS AND RADIATION IMAGING SYSTEM

(71) Applicant: CANON KABUSHIKI KAISHA, Tokyo (JP)

(72) Inventors: Minoru Watanabe, Honjo (JP); Keigo Yokoyama, Honjo (JP); Masato Ofuji, Takasaki (JP); Jun Kawanabe, Kumagaya (JP); Kentaro Fujiyoshi, Tokyo (JP); Hiroshi Wayama, Kawasaki (JP); Kazuya Furumoto, Honjo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/090,471

(22) Filed: Apr. 4, 2016

(65) Prior Publication Data
US 2016/0299239 A1 Oct. 13, 2016

(30) Foreign Application Priority Data
Apr. 9, 2015 (JP) ................. 2015-080435

(51) Int. Cl.
*H01L 27/146* (2006.01)
*G01T 1/24* (2006.01)
(Continued)

(52) U.S. Cl.
CPC ............. *G01T 1/247* (2013.01); *G01N 23/04* (2013.01); *H01L 27/14603* (2013.01);
(Continued)

(58) Field of Classification Search
CPC ................. G01T 1/24; H01L 27/14603; H01L 27/14658; H04N 9/045; H04N 5/378
See application file for complete search history.

(56) References Cited

U.S. PATENT DOCUMENTS

| 2010/0073527 A1* | 3/2010 | Ichimiya | ................. H04N 5/367 348/247 |
| 2012/0001080 A1* | 1/2012 | Okada | ...................... H04N 5/32 250/366 |

(Continued)

FOREIGN PATENT DOCUMENTS

| CN | 102315233 A | 1/2012 |
| CN | 102551767 A | 7/2012 |

(Continued)

*Primary Examiner* — Kiho Kim
(74) *Attorney, Agent, or Firm* — Canon U.S.A., Inc. IP Division

(57) ABSTRACT

A radiation imaging apparatus includes a first control line electrically connected to a control electrode of an imaging switching element, a second control line electrically connected to a control electrode of a detection switching element, a signal line electrically connected to a main electrode of the detection switching element, a capacitance line arranged to be capacitively coupled with the signal line, wherein the capacitance line is different from the first control line and the second control line, a driving unit electrically connected to the second control line and the capacitance line and configured to apply a voltage to the detection switching element and the capacitance line, and a control unit configured to control the driving unit to apply, in a case where an on-state or off-state voltage is applied to the detection switching element, a voltage having an opposite polarity to that of the voltage to the capacitance line.

15 Claims, 11 Drawing Sheets

(51) Int. Cl.
  *G01N 23/04*  (2006.01)
  *H04N 5/32*  (2006.01)
  *H04N 5/369*  (2011.01)
  *H04N 5/378*  (2011.01)

(52) U.S. Cl.
  CPC .. *H01L 27/14612* (2013.01); *H01L 27/14663* (2013.01); *H04N 5/32* (2013.01); *H04N 5/3696* (2013.01); *H04N 5/378* (2013.01)

(56) References Cited

U.S. PATENT DOCUMENTS

| | | | |
|---|---|---|---|
| 2012/0049077 A1* | 3/2012 | Okada | H01L 27/14603 250/370.08 |
| 2012/0288061 A1* | 11/2012 | Okada | G01N 23/04 378/62 |
| 2013/0003926 A1* | 1/2013 | Okada | G01T 1/2928 378/62 |
| 2013/0009065 A1* | 1/2013 | Okada | H04N 5/32 250/363.01 |
| 2013/0009069 A1* | 1/2013 | Okada | G01T 1/243 250/370.09 |
| 2013/0075620 A1* | 3/2013 | Nishino | A61B 6/548 250/394 |
| 2013/0206998 A1* | 8/2013 | Oda | G01T 1/17 250/394 |
| 2014/0021360 A1 | 1/2014 | Oda | |
| 2014/0021365 A1* | 1/2014 | Oda | G01T 1/17 250/395 |
| 2014/0084175 A1* | 3/2014 | Ito | H04N 5/32 250/370.09 |
| 2015/0043715 A1* | 2/2015 | Kuwabara | H04N 5/32 378/62 |
| 2015/0192684 A1* | 7/2015 | Ito | A61B 6/542 250/362 |
| 2015/0215554 A1* | 7/2015 | Toyoguchi | H04N 5/3696 348/301 |
| 2016/0172399 A1* | 6/2016 | Nakata | H01L 27/14621 348/308 |

FOREIGN PATENT DOCUMENTS

| | | |
|---|---|---|
| CN | 103126698 A | 5/2013 |
| CN | 103369258 A | 10/2013 |
| JP | 2012-15913 A | 1/2012 |

* cited by examiner

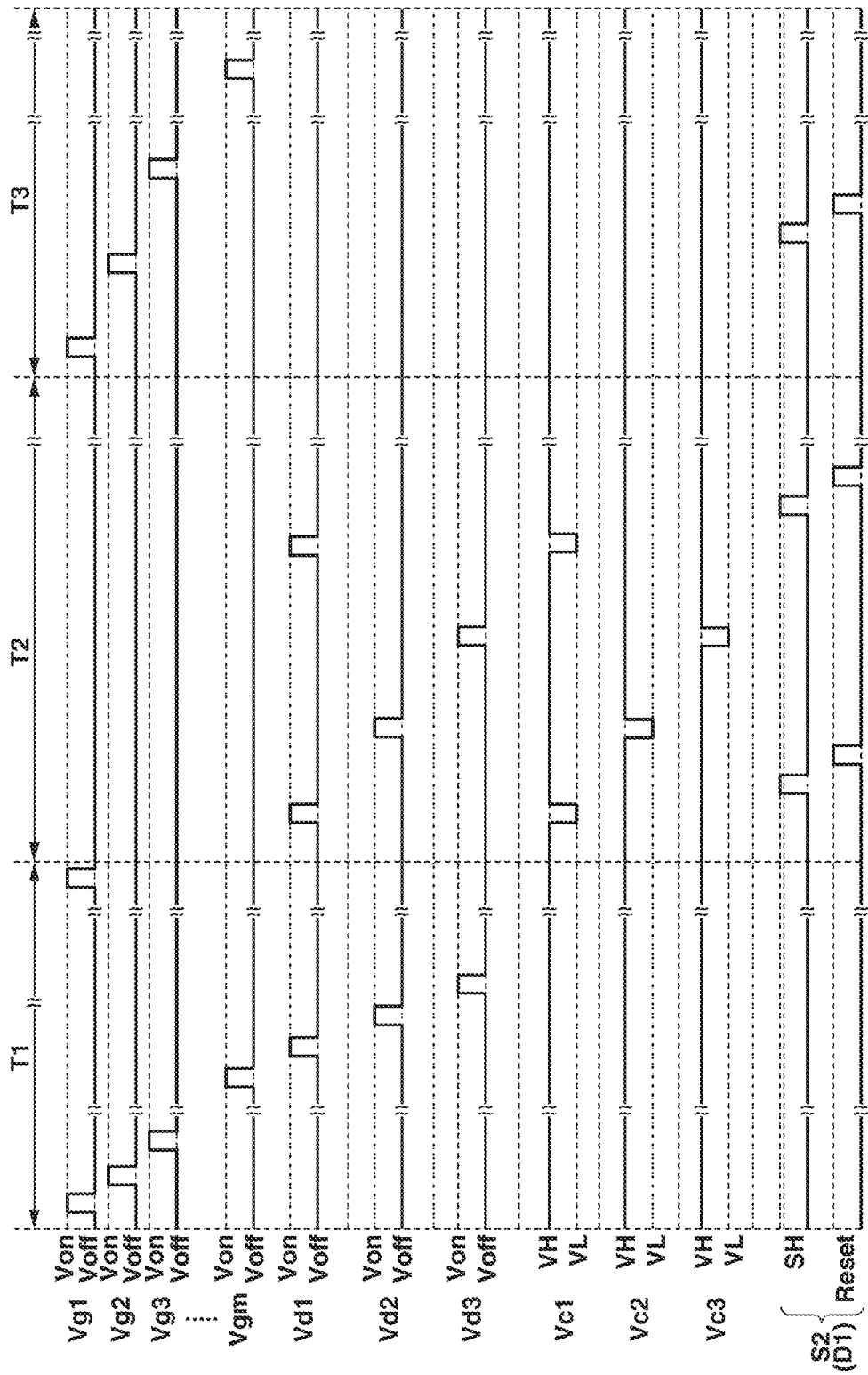

RADIATION IMAGING APPARATUS AND RADIATION IMAGING SYSTEM

BACKGROUND OF THE INVENTION

Field of the Invention

The present invention relates to a radiation imaging apparatus and a radiation imaging system.

Description of the Related Art

As a radiation imaging apparatus used for medical image diagnosis and non-destructive inspection by using radiation such as an X-ray, a radiation imaging apparatus including a matrix substrate having a pixel array obtained by combining switches including thin film transistors (TFTs) and conversion elements including photoelectric conversion elements has been put into practical use.

In recent years, multi-functionalization of the radiation imaging apparatus has been studied. As one type of the multi-functionalization, it has been studied that the radiation imaging apparatus has a built-in function of monitoring radiation irradiation. This function enables detection of a timing at which radiation irradiation from a radiation source has been started, detection of a timing at which radiation irradiation is to be stopped, and detection of an irradiation amount or an integrated irradiation amount of radiation, for example.

Japanese Patent Application Laid-Open No. 2012-15913 discusses a radiation imaging apparatus including imaging pixels for acquiring a radiation image and detection pixels for detecting radiation, and further discusses a configuration in which a signal for detecting radiation is read out via a switching element connected to the each detection pixel. To switch a conductive state of the switching element when a signal is read out of the detection pixel, a driving voltage is switched between a conductive voltage and a non-conductive voltage, as needed, to switch a conductive state of the switching element.

However, in the radiation imaging apparatus discussed in Japanese Patent Application Laid-Open No. 2012-15913, when the driving voltage is switched, a signal to be transmitted to a signal line may vary due to a parasitic element (parasitic capacitance) between a control line connected to the switching element and a signal line as a voltage on the control line changes. Therefore, the detection accuracy of radiation irradiation may be low depending on a potential variation on the signal line.

SUMMARY OF THE INVENTION

The present invention is directed to a technique capable of suppressing a potential variation occurring on a signal line due to switching of a control signal to a switching element in radiation detection pixels and of reading out radiation irradiation with high accuracy.

According to an aspect of the present invention, a radiation imaging apparatus includes an imaging pixel configured to acquire a radiation image, wherein the imaging pixel includes an imaging switching element for outputting a signal from an imaging conversion element, a detection pixel configured to detect radiation incidence, wherein the detection pixel includes a detection switching element for outputting a signal from a detection conversion element, a first control line electrically connected to a control electrode of the imaging switching element, a second control line electrically connected to a control electrode of the detection switching element, a signal line electrically connected to a main electrode of the detection switching element, a capacitance line arranged to be capacitively coupled with the signal line, wherein the capacitance line is different from the first control line and the second control line, a driving unit electrically connected to the second control line and the capacitance line and configured to apply a voltage to the detection switching element and the capacitance line, and a control unit configured to control the driving unit to apply, in a case where an on-state or off-state voltage is applied to the detection switching element, a voltage having an opposite polarity to that of the voltage to the capacitance line.

Further features of the present invention will become apparent from the following description of exemplary embodiments with reference to the attached drawings.

BRIEF DESCRIPTION OF THE DRAWINGS

FIG. 10 is a timing chart illustrating an operation of the radiation imaging apparatus according to the second exemplary embodiment.

DESCRIPTION OF THE EMBODIMENTS

Exemplary embodiments of the present invention will be described below with reference to the accompanying drawings. In each of the exemplary embodiments, "radiation" includes, in addition to an α beam, a β beam, and a γ beam, which is a beam generated by particles (including photons) emitted due to radiation destruction, a beam having substantially the same or more energy, e.g., an X-ray, a particle beam, and a cosmic ray.

Figure 1:
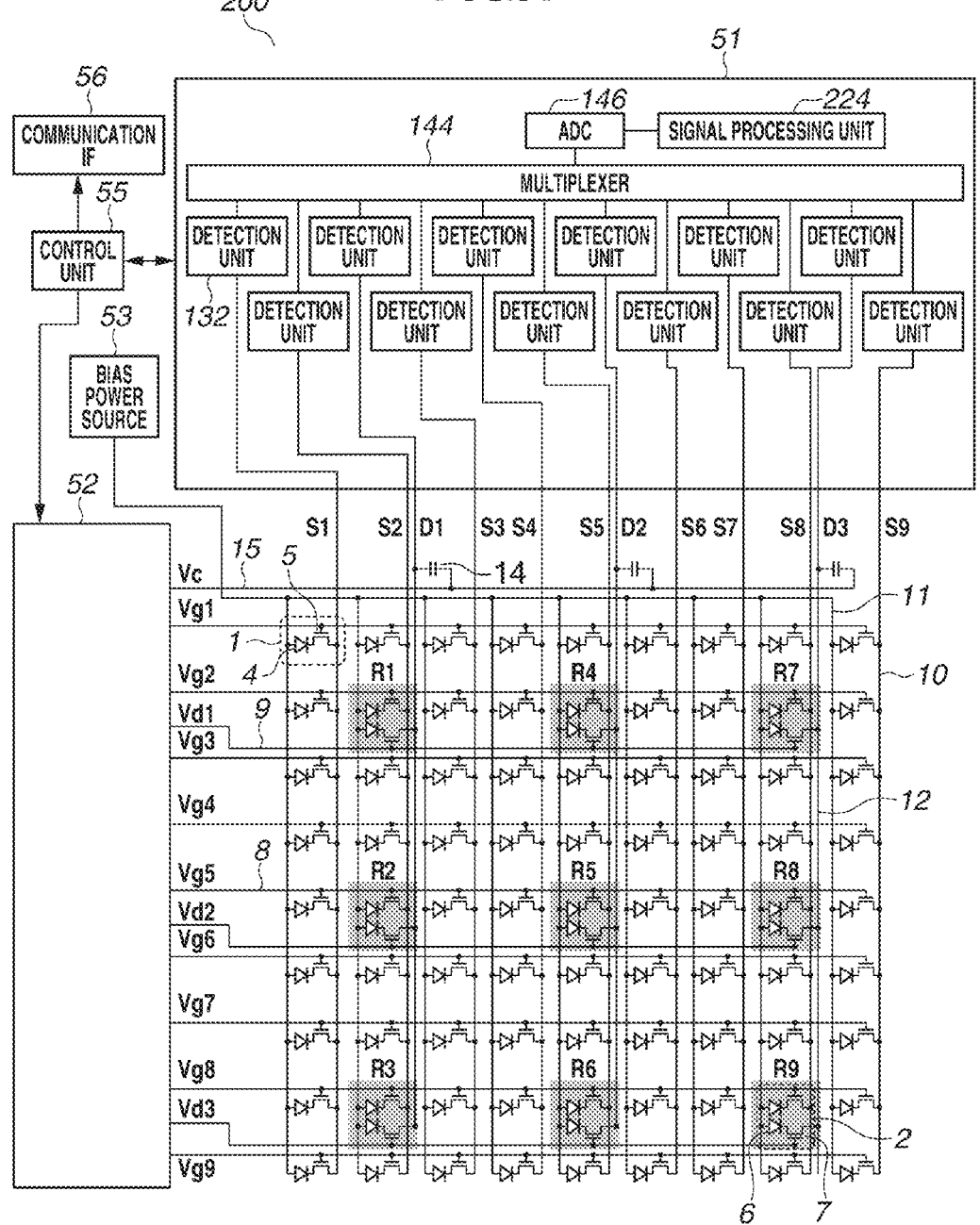
FIG. 1 is a block diagram illustrating a configuration of a radiation imaging apparatus according to a first exemplary embodiment.

A first exemplary embodiment will be described with reference to FIG. 1. FIG. 1 illustrates a configuration of a radiation imaging apparatus according to the first exemplary embodiment. While an example in which pixels in nine rows and nine columns are provided is illustrated in FIG. 1, 1000×1000 pixels may be provided. Alternatively, 5000×5000 pixels may be provided.

A radiation imaging apparatus 200 illustrated in FIG. 1 includes a plurality of imaging pixels 1 (hereinbelow, sometime refers to "imaging pixel 1" for the convenience of description) for acquiring a radiation image, and a plurality of detection pixels 2 (hereinbelow, sometime refers to "detection pixel 2" for the convenience of description) each including a detection conversion element 6 for detecting radiation incidence and a second switching element 7 connected to the detection conversion element 6. Further, the radiation imaging apparatus 200 includes at least a second control line 9 and a driving unit 52. Further, the radiation imaging apparatus 200 includes a capacitance line 15. The capacitance line 15 is arranged so that a capacitively coupled portion (a capacitative element 14) is formed between a detection signal line 12 and itself. As one example of the arrangement, the capacitance line 15 can form the capacitative element 14 by being arranged to intersect the detection signal line 12 via a dielectric body such as an insulating member, for example. The capacitance line 15 is electrically connected to the driving unit 52. The capacitative element 14 is an example illustrating a portion capacitively coupled between the capacitance line 15 and the detection signal line 12. Therefore, the capacitative element 14 can include a parasitic capacitance generated between a portion formed as a passive element and the detection signal line 12. The capacitance line 15 is provided as a wiring different from at least a first control line 8 and the second control line 9.

In the following description, among the plurality of imaging pixels 1 and the plurality of detection pixels 2, an array of the pixels lining up in a direction in which a signal line 10 extends is a column direction, and an array of the pixels lining up in a direction perpendicular to the column direction is a row direction.

The imaging pixel 1 is a pixel for acquiring the radiation image, and includes an imaging conversion element 4 and a first switching element 5. The detection pixel 2 is a pixel having a function of detecting radiation incidence, and includes the imaging conversion element 4, the first switching element 5, the detection conversion element 6, and the second switching element 7. Thus, in the present exemplary embodiment, the detection pixel 2 has a function of detecting radiation incidence and a function of acquiring a radiation image. While the detection pixel 2 has been described as including the imaging conversion element 4 and the first switching element 5, the detection conversion element 6, and the second switching element 7, the present invention is not limited thereto. For example, the detection element 2 may include only the detection conversion element 6 and the second switching element 7. The detection conversion element 6 in the detection pixel 2 in this case may be arranged in the same size as that of the imaging conversion element 4 in the imaging pixel 1. An imaging switching element in the present invention corresponds to the first switching element 5 in the present exemplary embodiment. A detection switching element in the present invention corresponds to the second switching element 7 in the present exemplary embodiment.

Each of the imaging conversion element 4 and the detection conversion element 6 can include a scintillator (not illustrated) that converts radiation into light and a photoelectric conversion element that converts light into an electric signal. The scintillator is formed in a sheet shape to cover an imaging region and is shared between the plurality of imaging pixels 1 and the plurality of detection pixels 2 as one example. Alternatively, each of the imaging conversion element 4 and the detection conversion element 6 can include a conversion element that directly converts radiation into an electric signal. Thus, the imaging region can be a region that can be converted into an image by a radiation imaging apparatus when radiation is incident thereon and a region that can detect the radiation incidence.

The first switching element 5 has a function of outputting a signal from the imaging conversion element 4. The second switching element 7 has a function of outputting a signal from the detection conversion element 6. Each of the first switching element 5 and the second switching element 7 can include a thin film transistor (TFT) including an active region composed of a semiconductor such as amorphous silicon or polycrystalline silicon (polysilicon), for example.

The imaging conversion element 4 is connected to a reading unit 51 via the first switching element 5 and the signal line 10 (S1 to S9). The detection conversion element 6 is connected to the reading unit 51 via the second switching element 7 and the detection signal lines 12. The detection signal line 12 is common to and connected to the respective second switching elements 7 in the plurality of detected pixels 2 as one example. In this way, each of the switching elements operates to output a signal from the conversion element connected thereto depending on a drive state.

All the pixels are connected to a common bias wiring 11, and a predetermined bias voltage is applied thereto from a bias power source 53. The first switching element 5 arranged in a predetermined row is connected to the first control line 8 (Vg1 to Vg9). The second switching element 7 is connected to the second control line 9 (Vd1 to Vd3).

The capacitance line 15 is arranged outside a region (imaging region) where the plurality of imaging pixels 1 is arranged. The capacitance line 15 is arranged in the same direction as the first control line 8 and/or the second control line 9. In the present exemplary embodiment, the capacitance line 15 is arranged to be parallel with the first control line 8 or the second control line 9. In the present exemplary embodiment, the arrangement of the capacitance line 15 is not limited thereto. The capacitance line 15 may be arranged in such a manner that the capacitative element 14 is formed between the detection signal line 12 and itself.

The radiation imaging apparatus 200 illustrated in FIG. 1 is provided with nine radiation detection regions (Region of Interest (ROI)) used when detecting radiation (R1 to R9 in FIG. 1). The detection pixel 2 is arranged in each of the radiation detection regions (ROI). The respective detection pixels 2 in the radiation detection regions R1, R2, and R3 are connected to the common detection signal line 12 (D1 in FIG. 1). Similarly, the respective detection pixels 2 in the radiation detection regions R4, R5, and R6 are connected to the common detection signal line 12 (D2 in FIG. 1), and respective detection pixels 2 in the radiation detection regions R7, R8, and R9 are connected to the common detection signal line 12 (D3 in FIG. 1). While an example in which the one detection pixel 2 is arranged in each of the radiation detection regions (ROI) has been described in the present exemplary embodiment, the plurality of detection pixels 2 may be arranged in one of the radiation detection regions (ROI). As one example, the plurality of detection pixels 2 may be connected and arranged in a row or column direction. In this case, the detection pixels 2 are desirably in at least a regular arrangement in the row or column direction or an oblique direction in the radiation detection region (ROI). The regular arrangement can include not only a case where the detection pixels 2 are continuously arranged but also a case where the imaging pixels 1 and the detection pixels 2 are arranged with predetermined spacing in the radiation detection region (ROI). While the nine (three× three) radiation detection regions (ROI) are arranged in FIG.

1, the present invention is not limited thereto. For example, 25 (five×five) radiation detection regions (ROI) may be provided, or 100 (10×10) radiation detection regions (ROI) may be provided. The radiation detection regions (ROI) may be uniformly arranged on a substrate, or may be non-uniformly arranged in a specific range. An arrangement of the imaging pixels 1 and the detection pixels 2 is an example. The present invention is not limited to the arrangement.

The reading unit 51 can include a plurality of detection units 132, a multiplexer 144, and an analog-to-digital converter 146 (hereinafter referred to as an ADC). Each of the plurality of signal lines 10 and the plurality of detection signal lines 12 is connected to the corresponding detection unit 132 in the reading unit 51. The signal line 10 or the detection signal line 12 has a one-to-one correspondence with the detection unit 132. Therefore, the reading unit 51 can be controlled not to operate the detection unit 132 corresponding to the detection signal line 10 during a waiting time until radiation is incident thereon. As a result, in the radiation imaging apparatus 200, power consumption can be further reduced and heat generation can also be further suppressed than a case where the detection unit 132 common between the signal line 10 and the detection signal line 12 is provided. For example, in an apparatus having a built-in battery, for example, a portable type radiation imaging apparatus, consumption of the battery can be suppressed. The detection unit 132 includes a differential amplifier and a sample-and-hold circuit (not illustrated), for example. The detection unit 132 can acquire a signal by performing sampling and holding using the sample-and-hold circuit. The multiplexer 144 selects the plurality of detection units 132 in a predetermined order, and feeds a signal from the selected detection unit 132 to the ADC 146. The ADC 146 converts the fed signal into a digital signal, and outputs the digital signal. The output of the ADC 146 is fed to a signal processing unit 224, and is processed by the signal processing unit 224. The signal processing unit 224 outputs information representing radiation irradiation onto the radiation imaging apparatus 200 based on the output of the ADC 146. More specifically, the signal processing unit 224 detects radiation irradiation onto the radiation imaging apparatus 200 and calculates an irradiation amount and/or an integrated irradiation amount of radiation, for example.

The driving unit 52 is electrically connected to each of the first control line 8, the second control line 9, and the capacitance line 15. In the present exemplary embodiment, the driving unit 52 outputs an on-state voltage for causing the first switching element 5 and the second switching element 7 to be conductive and an off-state voltage for causing the first switching element 5 and the second switching element 7 to be non-conductive. Thus, the driving unit 52 applies a voltage for controlling an output by the first switching element 5 via the first control line and applies a voltage for controlling an output by the second switching element 7 via the second control line 9. Further, the driving unit 52 applies a voltage to the capacitative element 14 via the capacitance line 15.

In the present exemplary embodiment, "driving" means controlling each of the switching elements to be conductive or non-conductive, and causing the capacitative element 14 to generate a charge.

Further, a capacitative element driving unit 54 may be provided separately from the driving unit 52 to drive the capacitative element 14. Details will be described in a second exemplary embodiment.

A control unit 55 can control the driving unit 52 and the reading unit 51. The control unit 55 controls the start and the end of exposure (storage of a charge corresponding to irradiated radiation on the imaging pixel 10), for example, based on the information from the signal processing unit 224. Thus, the control unit 55 can measure and acquire an incidence amount of radiation detected by the detection conversion element 6 based on an amount of the radiation.

When an irradiation amount of radiation is measured, the driving unit 52 applies an on-state voltage to the second switching element 7 via the second control line 9. In this case, a potential variation occurs via the second switching element 7 and a parasitic capacitance $C_{gs}$ at an intersection of the second control line 9 and the detection signal line 12. In this case, a charge Q (injection charge) expressed by $Q=(V_{on}-V_{off})\times C_{gs}$ is generated on the detection signal line 12. A feedback capacitance of a first-stage operational amplifier in the detection unit 132 may be saturated by the charge Q. As a result, the detection accuracy of the irradiation amount of the radiation by the detection unit 132 may be decreased. As one example, when a charge stored in the detection conversion element 6 is read out at short intervals, the decrease in the detection accuracy becomes significant if the detection unit 132 is driven with the feedback capacitance thereof decreased and the gain thereof increased.

A case where a plurality of (e.g., 10) detection pixels 2 is arranged in the column direction in each of the radiation detection regions (ROI) will be further described. When the reading unit 51 simultaneously reads out respective signals from the plurality of detection conversion elements 6, the effect of the charge Q becomes significant because the number of the signals read out at one time by the reading unit 51 increases while the injection charge increases in proportion to the magnitude of the parasitic capacitance $C_{gs}$ between the second control line 9 and the detection signal line 12.

Therefore, when the voltage applied to the second switching element 7 via the second control line 9 by the driving unit 52 is changed, the driving unit 52 suppresses a signal variation caused by the charge generated on the detection signal line 12 via the parasitic capacitance $C_{gs}$ between the second control line 9 and the detection signal line 12. As one example, the driving unit 52 applies a voltage having an opposite polarity to that of a voltage applied to the second switching element 7 to the capacitative element 14 via the capacitance line 15 to cancel out the injection charge. Thus, the capacitative element 14 acts to generate the same charge as $(V_{on}-V_{off})\times C_{gs}$ whose positive and negative polarities are reversed. The capacitance of the capacitative element 14 is desirably equal to the parasitic capacitance $C_{gs}$, for example, and the voltage to be applied to the capacitative element 14 is desirably $(-V_{on}+V_{off})$. As one example, the capacitance of the capacitative element 14 may be approximately two times the parasitic capacitance $C_{gs}$, and a voltage to be applied to the capacitative element 14 may be $(\frac{1}{2})\times(-V_{on}+V_{off})$.

Figure 2:
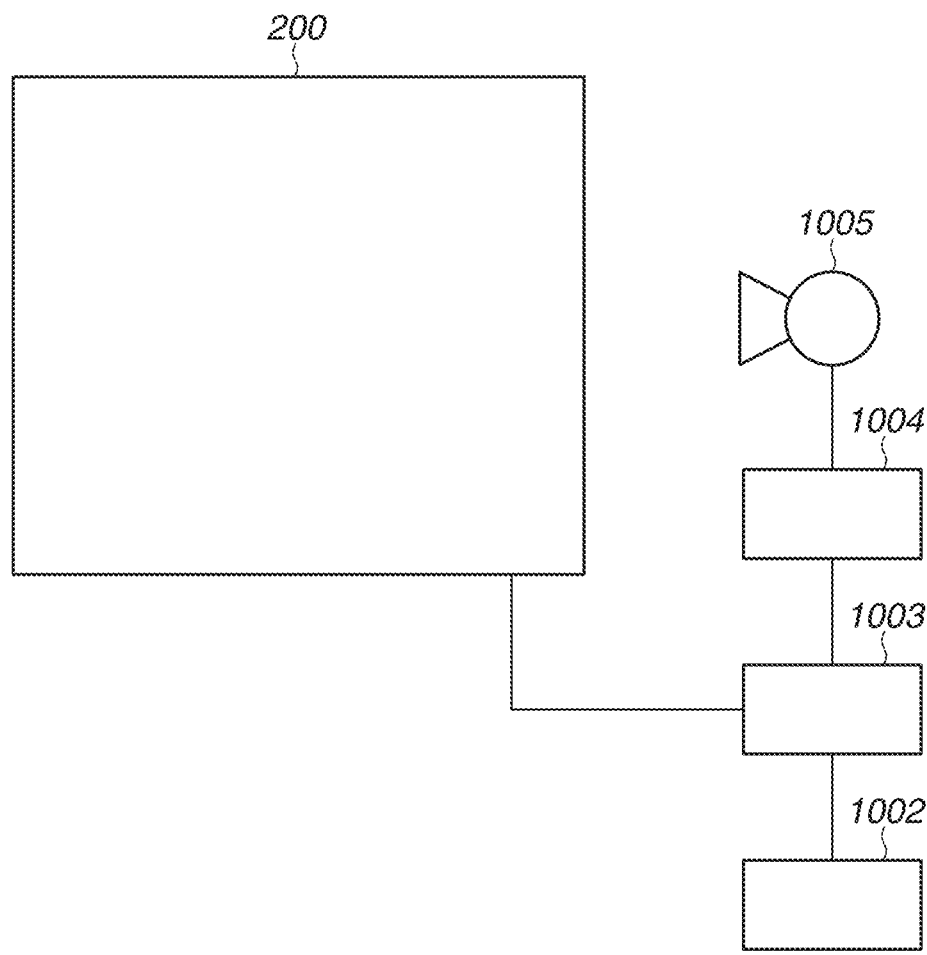
FIG. 2 is a block diagram illustrating a configuration example of a radiation imaging system including the radiation imaging apparatus.

FIG. 2 illustrates an example configuration of a radiation imaging system including the radiation imaging apparatus 200. The radiation imaging system includes a controller 1002, an interface 1003, a radiation source interface 1004, and a radiation source 1005 in addition to the radiation imaging apparatus 200.

A dose A, an irradiation time B (ms), a X-ray tube current C (mA), a tube voltage D (kV), and a radiation detection region (ROI) serving as a region where radiation is to be monitored are input to the controller 1002. When an exposure switch attached to the radiation source 1005 is operated, radiation is emitted from the radiation source 1005. The control unit 55 in the radiation imaging apparatus 200 feeds an exposure stop signal to the radiation source interface 1004 via the interface 1003 when an integrated value of a signal read out of the detection pixel 2 arranged in the radiation detection region (ROI) reaches a dose A', for example. In response thereto, the radiation source interface 1004 causes the radiation source 1005 to stop the radiation emission. The dose A' can be determined by the control unit 55 based on the dose A, a radiation irradiation intensity, and a communication delay and a processing delay between the units. If the irradiation time of the radiation reaches the irradiation time B, the radiation source 1005 stops emitting the radiation regardless of the presence or absence of the exposure stop signal.

Figure 3A:
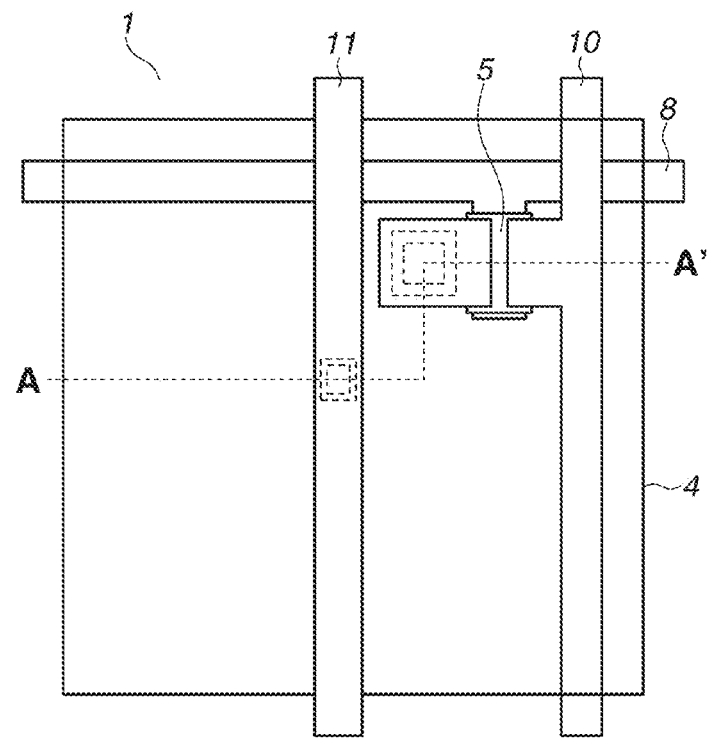
FIGS. 3A and 3B illustrate imaging pixels in a radiation imaging apparatus according to a first exemplary embodiment.
Figure 3B:
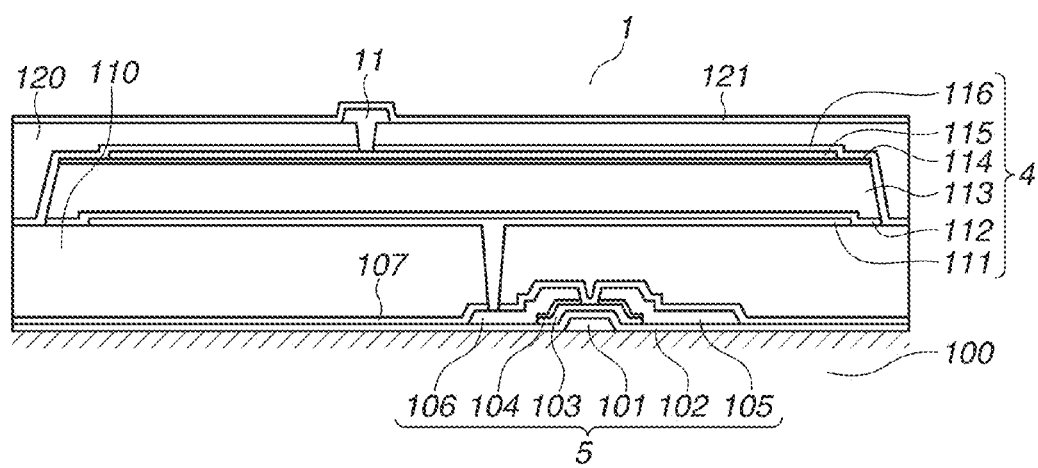

A configuration of an imaging pixel will be described below with reference to FIGS. 3A and 3B. FIG. 3A is a plan view of the imaging pixel 1, and FIG. 3B is a cross-sectional view taken along a line A-A' of the imaging pixel.

The imaging pixel 1 in the present exemplary embodiment includes an imaging conversion element 4 and a first switching element 5 that outputs an electric signal corresponding to a charge of the imaging conversion element 4. The imaging conversion element 4 is arranged in a state of being stacked on the first switching element 5 provided on an insulating substrate 100 such as a glass substrate with a first interlayer insulating layer 110 sandwiched therebetween. The first switching element 5 includes, on the substrate 100, a control electrode 101, a first insulating layer 102, a first semiconductor layer 103, a first impurity semiconductor layer 104 having a higher impurity concentration than that of the first semiconductor layer 103, a first main electrode 105, and a second main electrode 106 in this order from the side of the substrate 100. The first impurity semiconductor layer 104 contacts the first main electrode 105 and the second main electrode 106 in its partial region, and a region between a region, contacting the partial region, of the first semiconductor layer 103 and itself becomes a channel region of the first switching element 5. The control electrode 101 is electrically joined to a control line, the first main electrode 105 is electrically joined to the signal line 10, and the second main electrode 106 is electrically joined to individual electrodes 111 of the imaging conversion element 4. In the present exemplary embodiment, the first main electrode 105, the second main electrode 106, and the signal line 10 are integrally configured of the same conductive layer, and the first main electrode 105 constitutes a part of the signal line 10. A second insulating layer 107 and the first interlayer insulating layer 110 are arranged in this order from the side of the signal line 10 on the first main electrode 105, the second main electrode 106, and the signal line 10. While an inversely-staggered type switching element using a semiconductor layer and an impurity semiconductor layer mainly made of amorphous silicon has been used as the switching element in the present invention, the present invention is not limited thereto. For example, a staggered type switching element mainly made of polysilicon can be used, and an organic TFT and an oxide TFT can be used as the switching element. The first interlayer insulation layer 110 is arranged between the substrate 100 and the plurality of individual electrodes 111 to cover the first switching element 5, and has a contact hole. The individual electrodes 111 in the imaging conversion element 4 and the second main electrode 106 are electrically joined to each other in the contact hole provided in the first interlayer insulating layer 110. The imaging conversion element 4 includes, on the first interlayer insulating layer 110, the individual electrodes 111, a second impurity semiconductor layer 112, a second semiconductor layer 113, a third impurity semiconductor layer 114, and a common electrode 115 in this order from the side of the first interlayer insulating layer 110. A third insulating layer 116 is arranged on the common electrode 115 of the imaging conversion element 4. The common electrode 115 of the imaging conversion element 4 is electrically joined to a bias wiring 11 arranged on the second interlayer insulating layer 120. A fourth insulating layer 121 serving as a protective film is arranged on the bias wiring 11.

Figure 4A:
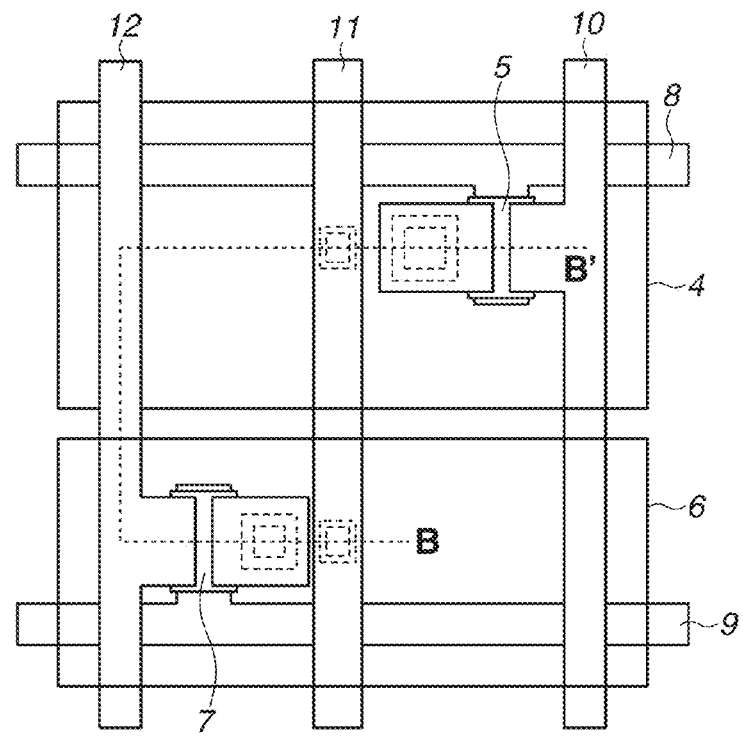
FIGS. 4A and 4B illustrates detection pixels in the radiation imaging apparatus according to the first exemplary embodiment.
Figure 4B:
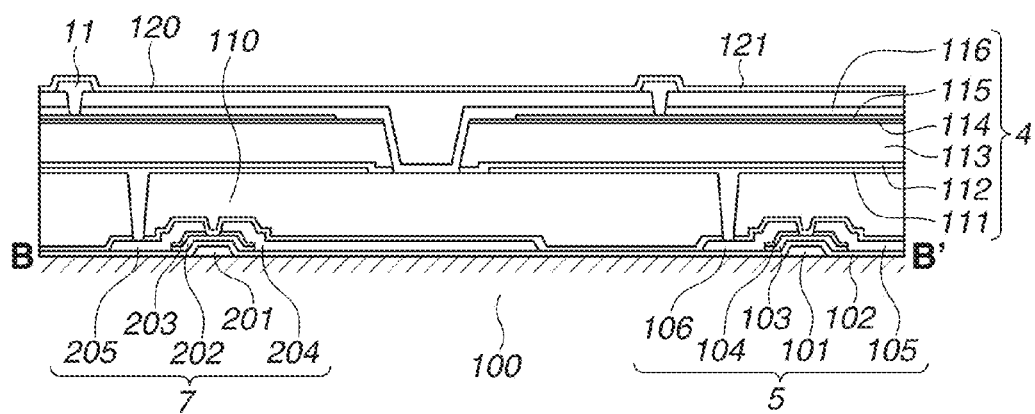

A configuration of the detection pixel 2 will be described below with reference to FIGS. 4A and 4B. FIG. 4A is a plan view of the detection pixel 2, and FIG. 4B is a cross-sectional view taken along a line B-B' of the detection pixel 2.

The detection pixel 2 in the present exemplary embodiment includes the imaging conversion element 4 and the first switching element 5, the detection conversion element 6, and the second switching element 7. The detection conversion element 6 is stacked on an upper layer of the first interlayer insulating layer 110 in a similar structure to that of the imaging conversion element 4 in the imaging pixel 1. The bias wiring 11 arranged on the second interlayer insulating layer 120 is electrically joined to the common electrode 115 between the imaging conversion element 4 and the detection conversion element 6. The individual electrodes 111 in the detection conversion element 6 are connected to the detection signal line 12 via the contact hole provided in the first interlayer insulating layer 110. The second insulating layer 107 and the first interlayer insulating layer 110 are arranged in this order from the side of the detection signal line 12 on the detection signal line 12. The second switching element 7 can take a similar structure to that of the first switching element 5. The second switching element 7 includes, on the substrate 100, a control electrode 201, a first insulating layer 102, a first semiconductor layer 202, a first impurity semiconductor layer 203 having a higher impurity concentration than that of the first semiconductor layer 202, a first main electrode 204, and a second main electrode 205 in this order from the side of the substrate 100. The first impurity semiconductor layer 203 contacts the first main electrode 204 and the second main electrode 205 in its partial region, and a region between a region, contacting the partial region, of the first impurity semiconductor layer 202 and itself becomes a channel region of the second switching element 7. The control electrode 201 is electrically joined to a control line, and the first main electrode 204 is electrically joined to the signal line 12.

The opening area of the imaging conversion element 4 in the detection pixel 2 becomes smaller than that in the imaging pixel 1 in the present exemplary embodiment. Therefore, a signal amount from the detection pixel 2 is decreased. An effect of this can be reduced by adjusting the gain of the detection unit 132 or correcting an image to be captured. The correction can be implemented by processing for interpolating the image to be captured using a value of the imaging pixel 1 around the detection pixel 2. While the imaging conversion element 4 and the detection conversion element 6 are respectively PIN type sensors in the present exemplary embodiment, the present invention is not limited thereto. An MIS type sensor and a TFT type sensor may be used.

Figure 5:
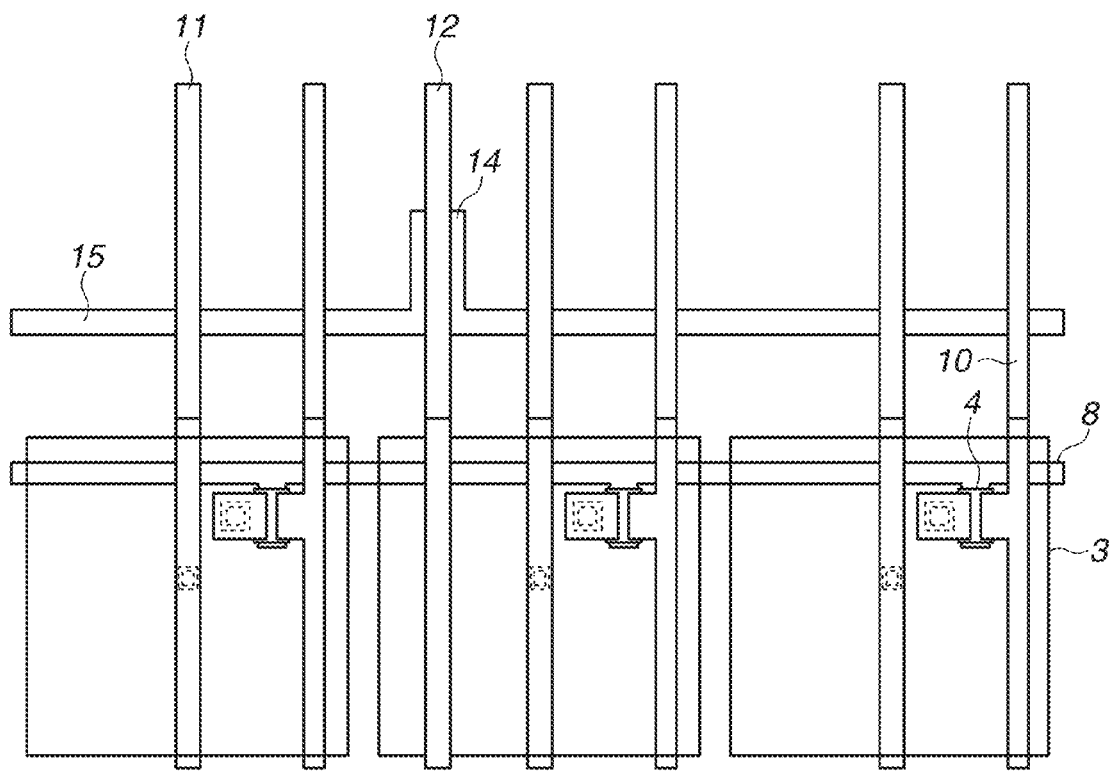
FIG. 5 illustrates a capacitative element in the radiation imaging apparatus according to the first exemplary embodiment and its vicinity.

A configuration of the capacitive element 14 will be described below with reference to FIG. 5. FIG. 5 illustrates the capacitive element 14 illustrated in FIG. 1 and its peripheral portion. A capacitance line 15 is arranged so that the capacitative element 14 is formed between the detection signal line 12 and itself.

The capacitance line 15 is preferably formed using the same metal layer as that of the second control line 9. This configuration enables the manufacturing process to be simplified because the capacitance line 15 can be formed in the same process as that for forming the second control line 9. The capacitative element 14 may be formed of a switching element and a photodiode, like the imaging pixel 1 and the detection pixel 2. As one example, the capacitative element 14 may include a switching element having the same structure as that of the first switching element 5 or the second switching element 7. In this case, the capacitative element 14 can be designed to have the parasitic capacitance Cgs with high accuracy, and thus a potential variation appearing on the detection signal line 12 when radiation is detected can be suppressed, as described above with high accuracy. The capacitative element 14 need not be formed using a semiconductor layer depending on the frequency of voltage applications. In this case, the capacitance is formed only by an insulating dielectric body. Therefore, an unstable phenomenon specific to a semiconductor element does not occur. Therefore, a stable operation can be performed. The unstable phenomenon includes a shift of a flat band voltage, for example.

Figure 6:
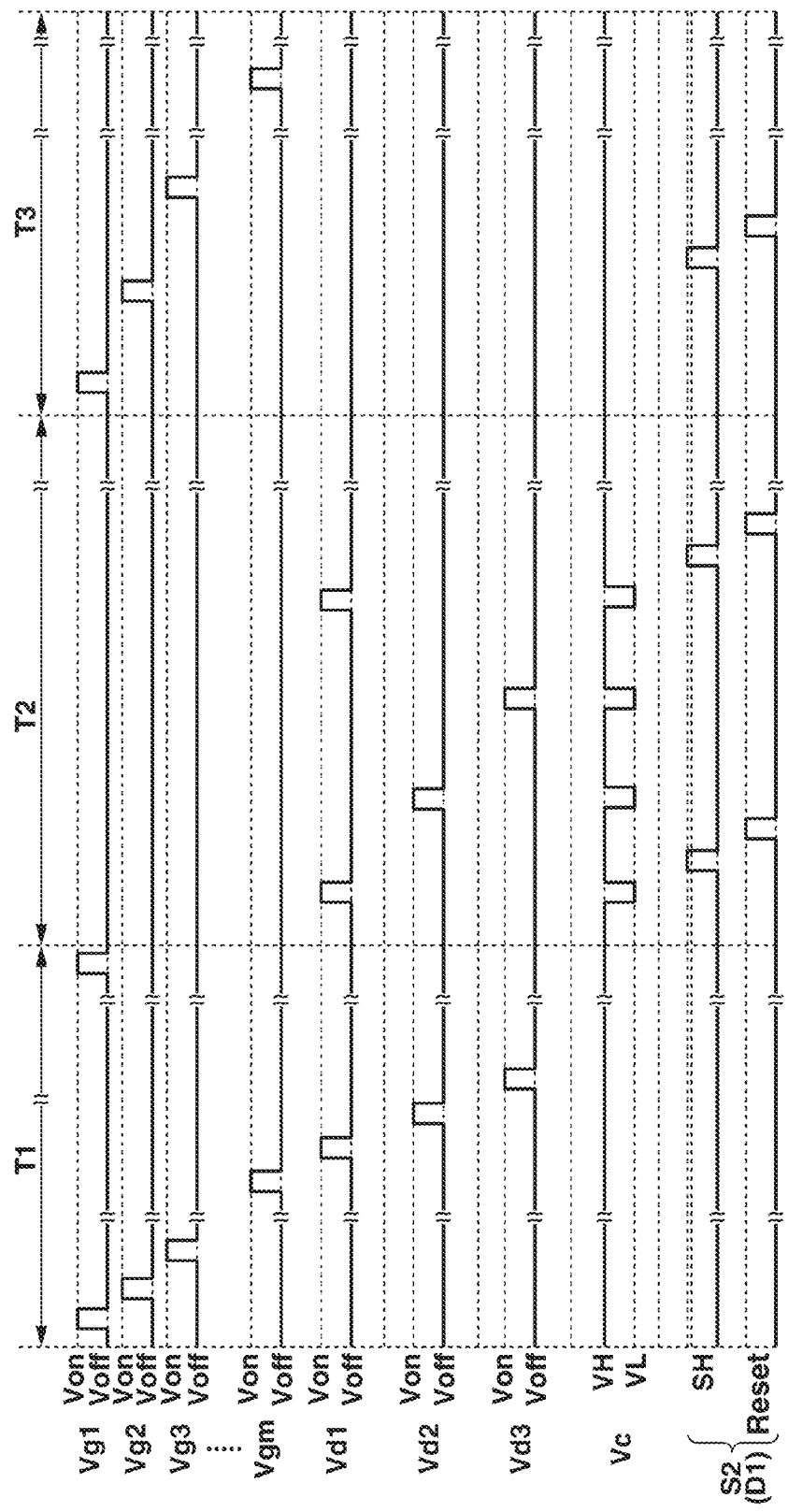
FIG. 6 is a timing chart illustrating an operation of the radiation imaging apparatus according to the first exemplary embodiment.

An operation of the radiation imaging apparatus according to the present exemplary embodiment will be described below with reference to a timing chart of FIG. 6. In the following description, voltages Vg1 to Vg9 are applied to the first control line 8 for driving the imaging pixel 1, and voltages Vd1 to Vd3 are applied to the second control line 9 for driving the detection pixel 2. The first switching element 5 and the second switching element 7 are caused to be conductive when a signal fed to the control electrode is at a high level, and are caused to be non-conductive when the signal fed to the control electrode is at a low level. A combination of the signal level and the conductive state can also be a combination that differs depending on a circuit configuration and the conductivity types of the switching elements. Respective operations of the reading unit 51 and the driving unit 52, illustrated in FIG. 6, are performed based on the control of the control unit 55, as described above. In FIG. 6, the high level is indicated by "Von", and the low level is indicated by "Voff". An "on-state voltage" in the present invention corresponds to "Von" in the present exemplary embodiment. An "off-state voltage" in the present invention corresponds to "Voff" in the present exemplary embodiment.

First, a period T1 illustrated in FIG. 6 will be described. The period T1 is a period during which the start of radiation irradiation is waited for. In the present exemplary embodiment, the period T1 is a period elapsed until an exposure switch in the radiation source 1005 is operated and the radiation irradiation is detected since the power to the radiation imaging apparatus 200 is turned on and a radiation image can be captured. In the period T1, a voltage Von is sequentially applied to the first switching element 5 and the second switching element 7, and the individual electrodes 111 of the imaging conversion element 4 and the detection conversion element 6 are respectively reset to potentials of the signal line 10 and the detection signal line 12. The voltage Von may always remain applied to the second switching element 7. In this way, a charge generated by a dark current is prevented from being stored over a long time in the imaging conversion element 4 of the imaging element 1. The length of the period T1 can be several seconds to several minutes, for example, although it greatly differs depending on an imaging method and an imaging condition.

Next, a period T2 illustrated in FIG. 6 will be described. The period T2 is a period during which radiation is being irradiated. As one example, the period T2 is a period elapsed until an exposure amount of the radiation reaches an optimum dose since the start of the radiation irradiation is detected. The period T2 can also be said to be a period during which an irradiation amount of the radiation is monitored. In the period T2, a voltage Voff1 is always applied as the voltages Vg1 to Vgm. Therefore, the first switching element 5 is caused to be non-conductive. The voltage Von is intermittently applied as the voltages Vd1 to Vd3, and the second switch 7 in the detection pixel 2 is intermittently caused to be conductive. In this case, an injection charge proportional to the parasitic capacitance Cgs between the second control line 9 and the detection signal line 12 appears on the detection signal line 12, as described above. Therefore, the detection accuracy of the radiation may be decreased caused by the injection charge. Further, the detection unit 132 connected to the detection signal line 12 may malfunction depending on the magnitude of the injection charge. Therefore, the driving unit 52 applies a voltage Vc having an opposite polarity to that of the voltages Vd1 to Vd3 to the capacitance line 15 connected to the capacitative element 14 when an on-state or off-state voltage is applied to the second control line 9. When a voltage VL is applied, a charge to cancel out the charge Q appearing on the detection signal line 12 is generated on the detection signal line 12. More specifically, the driving unit 52 applies the voltage VL having an opposite polarity to that of the voltage Von as the voltage Vc at a timing overlapping a timing at which the voltage Von is applied as the voltage Vd1, as illustrated in the period T2 in FIG. 6. While the overlapping timings are preferably the simultaneous timing, the present invention is not limited thereto. For example, if a charge injected due to a parasitic capacitance by applying the voltage Von or Voff to one of the second switches 7 connected to the detection signal line 12 can be substantially suppressed, the timings need not completely match each other. The charge caused by the parasitic capacitance Cgs can be substantially suppressed if an effect of the charge can be suppressed to such a degree that the detection accuracy is satisfied using the signal from the detection pixel 2 as a detection system. The effect of the parasitic capacitance Cgs and each of the voltages in the present exemplary embodiment will be described using equations. The charge Q generated on the detection signal line 12 via the parasitic capacitance Cgs when the second switching element 7 is driven is expressed by the following equation (1):

$$Q = (V\text{on} - V\text{off}) \times Cgs \quad (1)$$

A charge Q' generated by the capacitative element 14 is expressed by the following equation (2), where Cc is the capacitance of the capacitative element 14:

$$Q' = (VL - VH) \times Cc \quad (2)$$

The charge Q' required to cancel out the charge Q is desirably equal to the charge Q. Therefore, a capacitance value of the capacitative element 14 is desirably defined so that the following expression is satisfied:

$$(V\text{on} - V\text{off}) \times Cgs \approx (VL - VH) \times Cc \quad (3)$$

From the above described relationship, the following expression (4) is preferably satisfied, where Cgs is a capacitance formed between the second control line 9 and the detection signal line 12, $\Delta V$pp is a voltage difference applied to the second control line 9, Cc is a capacitance of the capacitively coupled portion (the capacitative element 14), and ΔVc is a voltage difference applied to the capacitance line 15:

$$\tfrac{1}{2} \times Cp \times Vpp < Cc \times \Delta Vc < 2 \times Cp \times Vpp \qquad (4)$$

Here VL−VH=ΔVc and Von−Voff =ΔVpp

The driving unit 52 desirably defines voltages respectively applied to the second switching element 7 and the capacitance line 15 to satisfy the foregoing equation. When the capacitance Cc and the voltage difference ΔVc are defined at least within a range of the foregoing expression, the injection charge Q can be preferably suppressed.

Next, a period T3 illustrated in FIG. 6 will be described below. The period T3 is a period during which a signal stored by radiation in the imaging pixel 1 is read out after the irradiation of radiation has been completed. In the period T3, the voltages Vd1 to Vdn are brought into a low level. In the period T3, the detection signal line 12 is preferably connected to a fixed potential to prevent the detection signal line 12 from floating. To scan the first control line 7, the voltage Von is sequentially applied as the voltages Vg1 to Vg9, and a signal stored in the imaging conversion element 4 is transferred to the reading unit 51 via the signal line 10.

Figure 7:
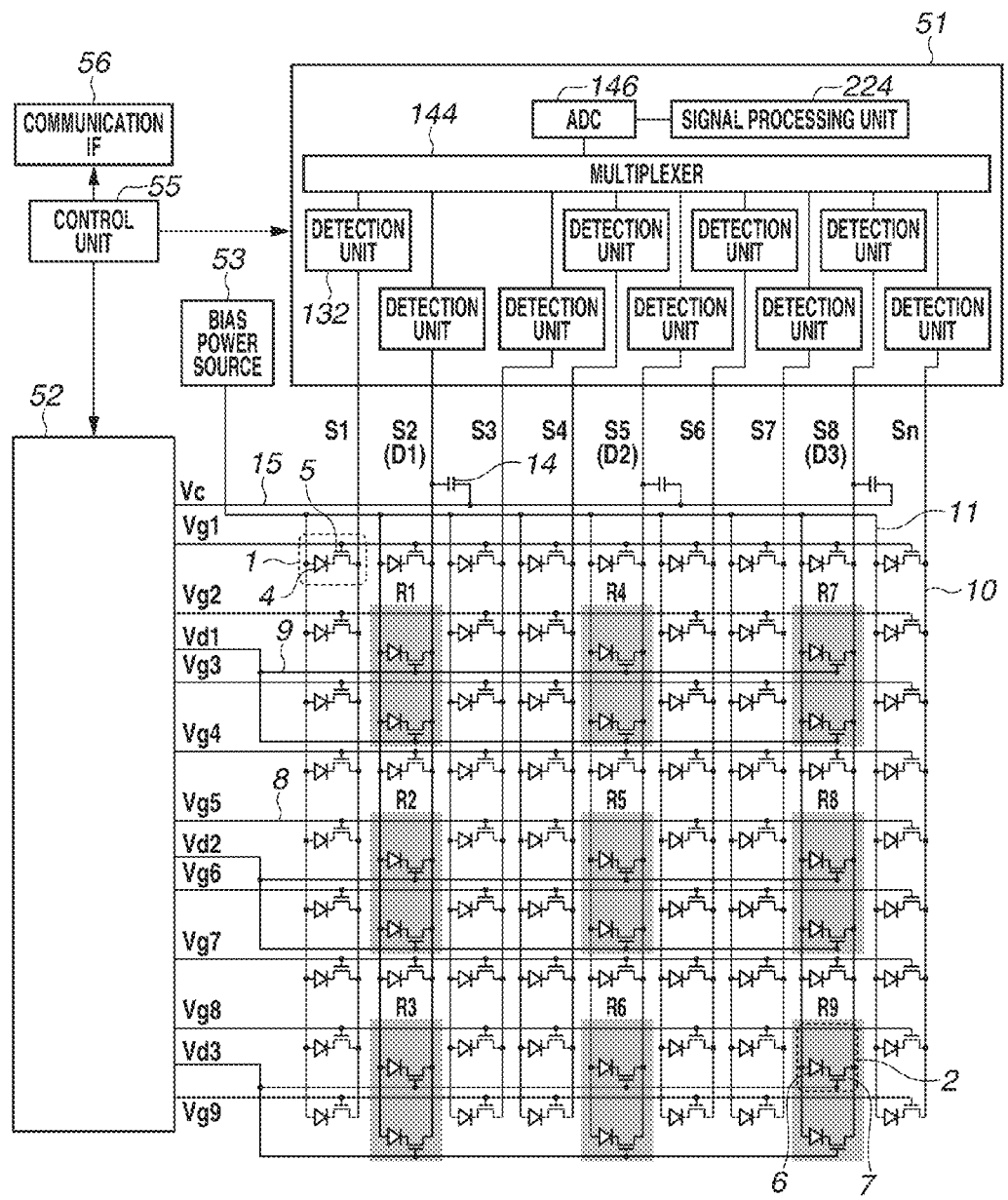
FIG. 7 is a block diagram illustrating another configuration example of the radiation imaging apparatus according to the first exemplary embodiment.

FIG. 7 illustrates another configuration example of the radiation imaging apparatus according to the present exemplary embodiment. As illustrated in FIG. 7, a plurality of detection pixels 2 is arranged in each of a plurality of detection regions (ROI). While two detection pixels 2 are arranged in one detection region as one example in FIG. 7, the present invention is not limited thereto. A plurality of detection pixels 2, e.g., three pixels, 10 pixels, and 20 pixels may be arranged. Second control lines 9 are bundled together between the driving unit 52 and the detection region and are connected to the plurality of detection pixels 2. The driving unit 52 can collectively drive the plurality of detection pixels 2 by outputting a voltage once. Thus, a wiring between the driving unit 52 and the detection region can be simplified. A period of time required for the driving unit 52 to acquire a signal in the detection region can be shortened. Detection conversion elements 6 are commonly connected to the signal line 10 within each of the detection regions. Thus, a signal from the detection conversion element 6 in each of the detection regions is doubled. On the other hand, the injection charge Q from each of the detection regions can be doubled.

Further, the detection pixel 2 includes a combination of the detection conversion element 6 and the second switching element 7, and does not include the imaging conversion element 4 and the first switching element 5. Further, the detection conversion element 6 is connected to the signal line 10 via the second switching element 7. Thus, a signal is read out of the detection pixel 2 via a signal line common between the imaging pixel 1 and the detection pixel 2. This configuration enables the detection sensitivity of radiation to be improved because the detection conversion element 6 can be arranged to be large in area. In this case, the detection pixel 2 becomes a defective pixel because the imaging conversion element 4 is not arranged therein. However, the detection pixel 2 can be corrected by complementing its data from an output and image data of the adjacent imaging pixel 1. The reading unit 51 can calculate (acquire) an incidence amount of the radiation in each of the detection regions based on a value obtained by adding or averaging values corresponding to signals acquired from the plurality of detection pixels 2 arranged in the detection regions. A configuration of the reading unit 51 can be more simplified than that of the radiation imaging apparatus 200 illustrated in FIG. 1.

Next, a configuration of the capacitative element 14 illustrated in FIG. 7 will be described below. As described above, in the case where the two detection conversion elements 6 are connected side by side in the column direction on the one detection signal line 12, the capacitative element 14 is arranged to have a capacitance that is two times a parasitic capacitance formed between the second control line 9 and the detection signal line 12 per pixel. The driving unit 52 outputs a voltage so that a voltage difference (VL−VH=ΔVc) between voltages VH and VL applied to the capacitance line 15 becomes equal to a voltage difference (Von−Voff=ΔVpp) applied to the second control line 9. The above described driving enables the driving unit 52 to cancel out a charge appearing on the detection signal line 12 due to the parasitic capacitance.

To suppress the above described effect, the driving unit can perform control to cancel out the injection charge Q by driving the capacitative element 14. Thus, the radiation imaging apparatus can improve a detection accuracy under the control. A malfunction of the reading unit 51 can be suppressed.

Figure 8:
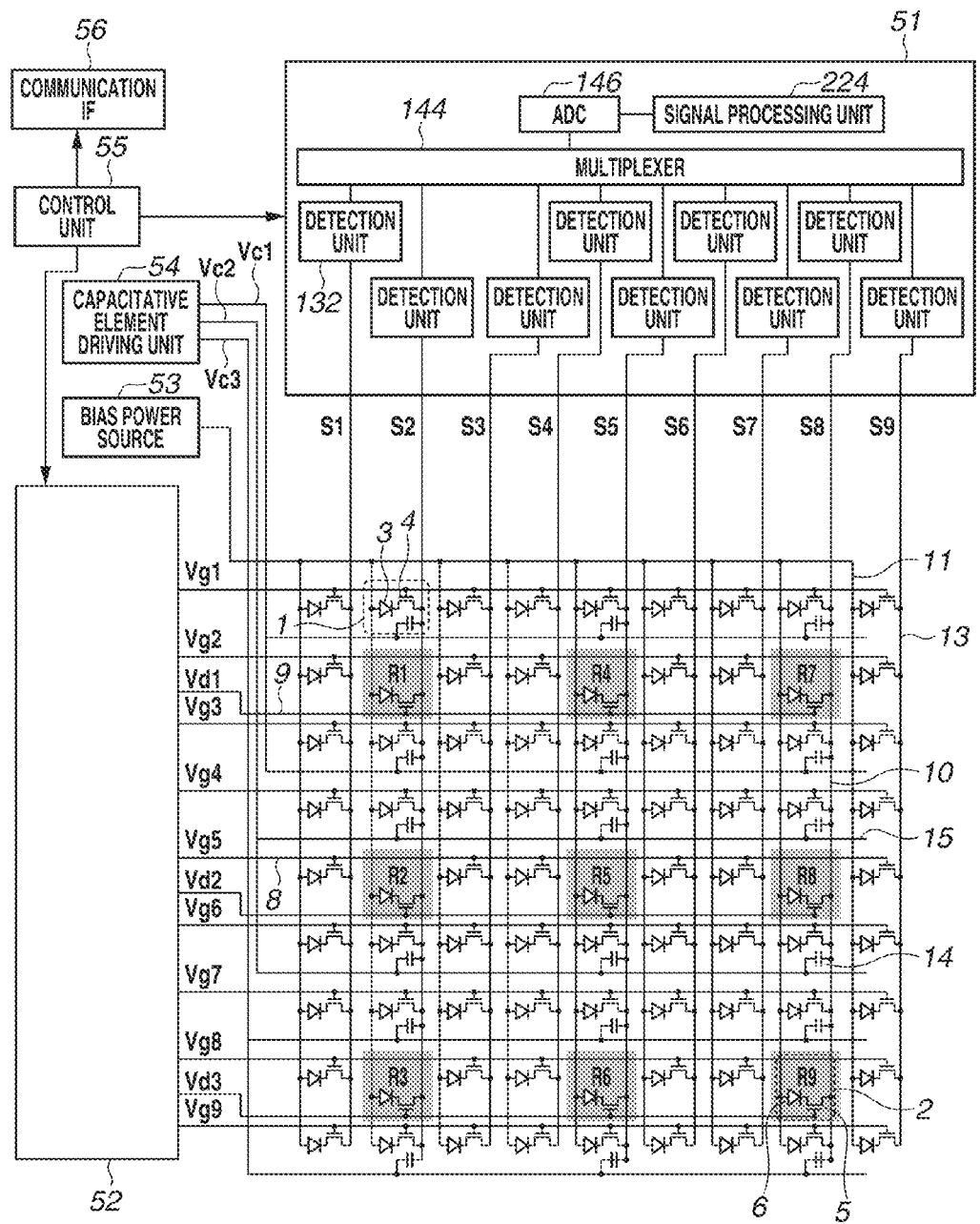
FIG. 8 is a block diagram illustrating a configuration of a radiation imaging apparatus according to a second exemplary embodiment.

A second exemplary embodiment will be described with reference to FIG. 8. FIG. 8 illustrates a configuration of a radiation imaging apparatus according to the second exemplary embodiment. The present exemplary embodiment differs from the first exemplary embodiment in that a capacitative element 14 is arranged in an imaging region where an imaging pixel is arranged. Details will be described below.

First, an arrangement of a capacitance line 15 will be first described. A plurality of capacitance lines 15 is arranged within the imaging region. Further, the capacitance lines 15 are arranged separately in upper and lower parts of each of the imaging regions. The capacitance lines 15 are arranged so that the capacitative elements 14 are formed in upper and lower parts of the imaging region. In the present exemplary embodiment, the capacitance lines 15 are arranged so that the capacitative elements 14 are uniformly arranged within the imaging region. However, the arrangement is one example. For example, the capacitance lines 15 may be arranged to be positioned at non-uniformly within the imaging region if an injection charge can be sufficiently suppressed at the position. Further, in the present exemplary embodiment, the radiation imaging apparatus includes a driving unit 52 that drives each of pixels and a capacitative element driving unit 54 that drives the capacitative elements 14.

When a voltage is applied to a second control line 9 and a voltage is applied to a second switching element 7, a charge (injection charge) caused by a parasitic capacitance appears on a signal line 10, as described in the first exemplary embodiment. In this case, a voltage waveform depending on a resistance value and a capacitance value of the second control line 9 and applied by the capacitative element driving unit 54 also changes between an input time and an output time. Therefore, an accuracy of suppressing the injection charge is decreased depending on the arrangement of the capacitative element 14. The capacitative element 14 is preferably arranged in the vicinity of a position where the injection charge is generated. In this case, the capacitance line 15 preferably has the same resistance value and capacitance value as those of the second control line 9. More specifically, the capacitance line 15 and the second control line 9 are preferably formed of materials having substantially the same lengths and substantially the same resistance values, respectively, and respective sites where the parasitic capacitance can be formed preferably have the same dielectric constant and the same thickness. Ranges "having substantially the same lengths and substantially the same resistance values" indicate that they are designed to be substantially the same to such a degree that the injection charge can be canceled out, need not be completely the same, and can also include a design error and a machine difference.

Figure 9A:
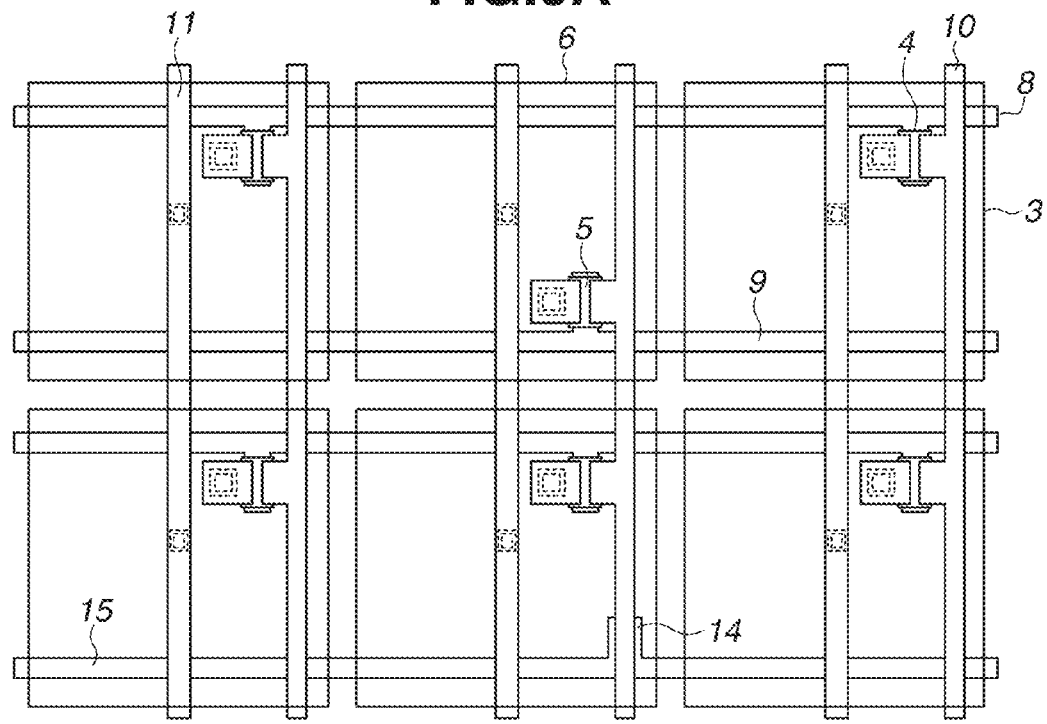
FIGS. 9A and 9B illustrate a capacitative element in the radiation imaging apparatus according to the second exemplary embodiment and its vicinity.
Figure 9B:
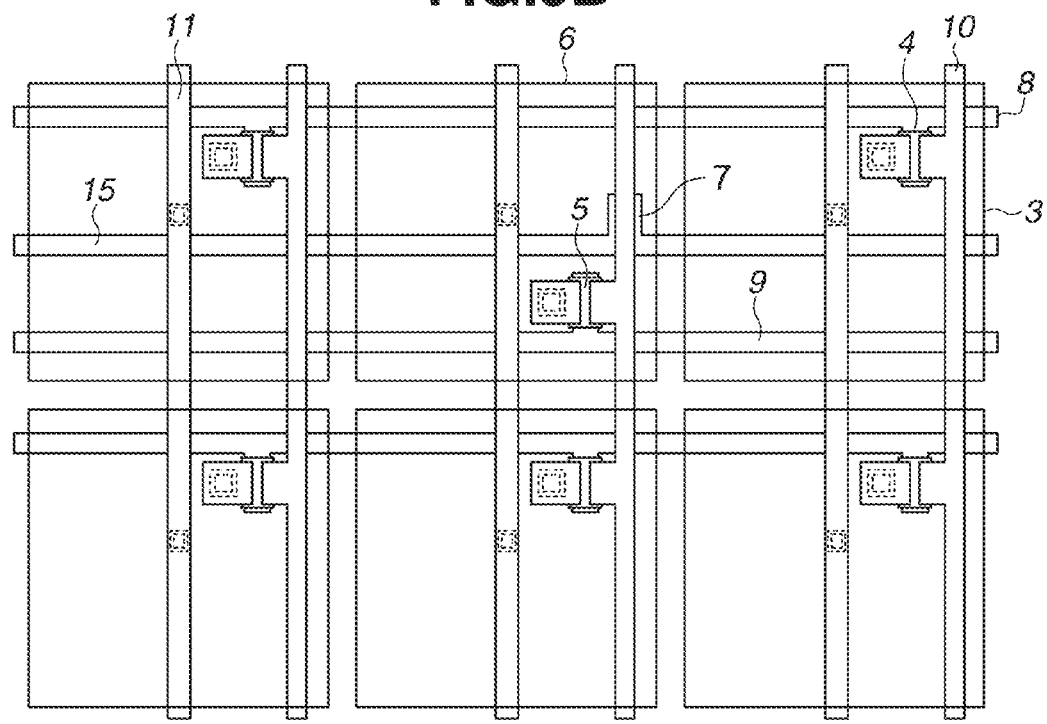

The capacitative element 14 in the present exemplary embodiment will be described with reference to FIGS. 9A and 9B. FIGS. 9A and 9B illustrate the capacitative element 14 in the present exemplary embodiment and its vicinity. The capacitative element 14 is formed between the signal line 10 and the capacitance line 15. The second exemplary embodiment differs from the first exemplary embodiment in that the capacitative element 14 is arranged adjacent to a detection conversion element 6. The capacitance line 15 is preferably formed of the same layer as that forming the second control line 9. The capacitance line 15 is formed in the same process as that for forming the second control line 9. Therefore, the capacitance line 15 can be formed without increasing the number of manufacturing steps.

FIG. 9B is a plan view illustrating the capacitative element 14 in the present exemplary embodiment and its periphery. FIG. 9B differs from FIG. 9A in that the capacitative element 14 is arranged in a row in which the second control line 9 serving as the site where the injection charge is generated is arranged. As a result, the injection charge can be more preferably suppressed.

An operation of the radiation imaging apparatus according to the present exemplary embodiment will be described below with reference to a timing chart of FIG. 10. In the following description, respective signs illustrated in FIG. 10 are the same in meaning as those illustrated in FIG. 6. Periods T1 and T3 are the same as those illustrated in FIG. 6, and hence description thereof is not repeated.

Next, a period T2 will be described below. First, to drive a second switching element 5, a voltage Von is applied to the second control line 9 as voltages Vd1 to Vd3. At this time, a charge Q proportional to a parasitic capacitance Cgs between the second control line 9 and the detection signal line 12 is generated on the detection signal line 12, so that a potential variation occurs. Due to the generation of the charge Q, the accuracy of radiation detection by a detection unit 132 may be decreased, and the detection unit 132 may malfunction. On the other hand, in the present exemplary embodiment, a voltage having an opposite polarity to that of an on-state or off-state voltage is applied to the capacitance line 15 close to the second control line 9 to be driven among the plurality of capacitance lines 15. The driving unit 52 can cancel out the charge Q generated on the signal line 10 due to the parasitic capacitance by applying a voltage having an opposite polarity to that of the voltages Vd1 to Vd3 to each of the capacitance lines 15. As described above, in the present exemplary embodiment, the capacitative element 14 is arranged in the imaging region where the imaging pixel is arranged, unlike that in the first exemplary embodiment. Therefore, the potential variation caused by the parasitic capacitance when the driving unit 52 applies the on-state or off-state voltage to a detection pixel 2 can be suppressed with high accuracy.

Example Application Embodiment

An example in which the radiation imaging apparatus 200 is applied to a radiation detection system will be described below with reference to FIG. 11.

Figure 11:
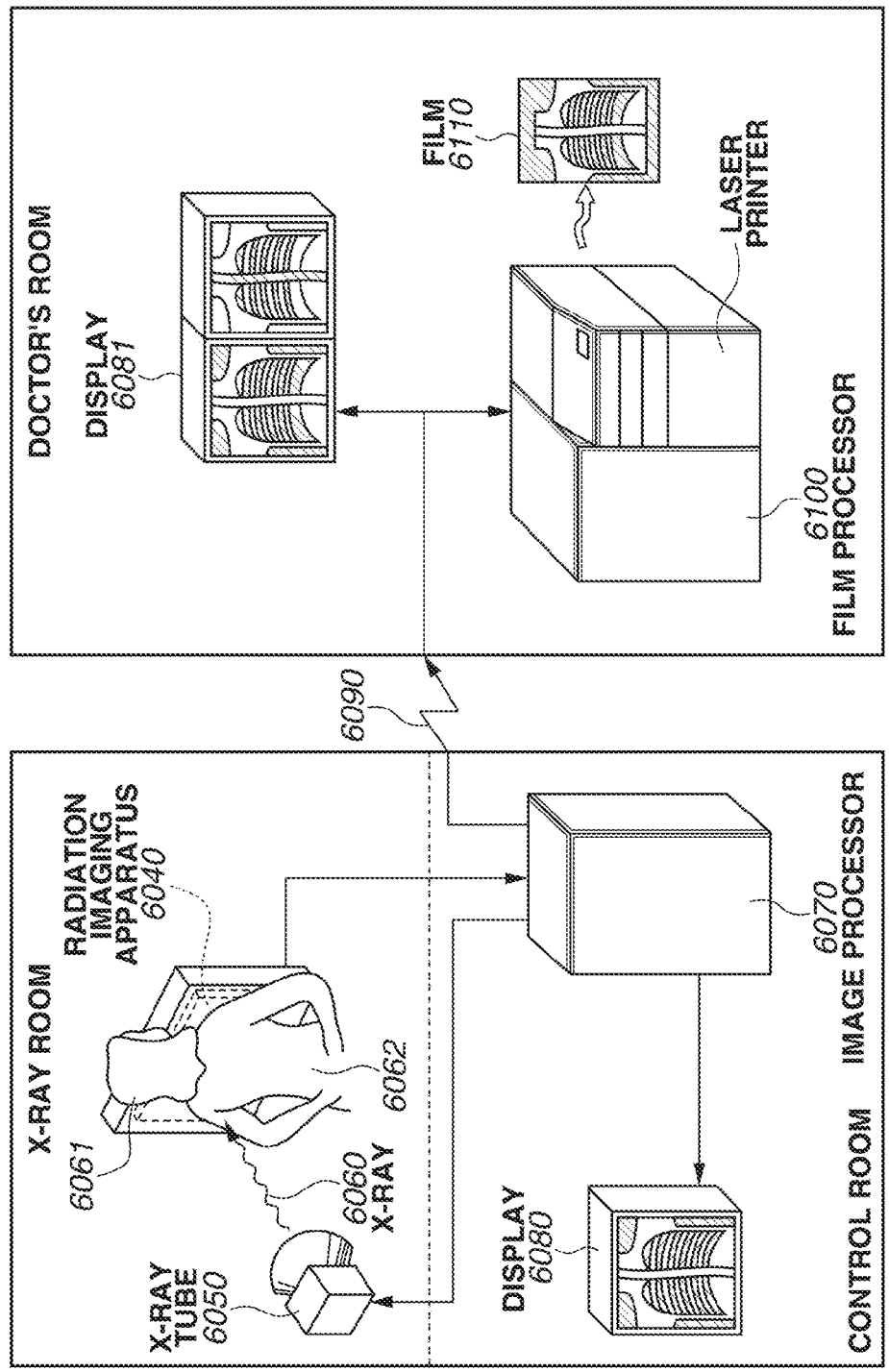
FIG. 11 illustrates an application example of the radiation imaging apparatus.

An X-ray 6060 generated by an X-ray tube 6050 serving as a radiation source is transmitted through a breast portion 6062 of a subject 6061, and is incident on the radiation imaging apparatus 200 or 6040 as illustrated in FIG. 11. Information about the inside of the body of the subject 6061 is included in the incident X-rays 6060. A conversion unit 3 converts radiation into a charge corresponding to the incidence of the X-rays 6060, to obtain electric information. This information is converted into digital data, and is subjected to image processing by an image processor 6070 serving as a signal processing unit, and can be observed by a display 6080 serving as a display unit in a control room.

This information can be transferred to a remote place by a transmission processing means such as a telephone line 6090, can be displayed on a display 6081 serving as a display unit in another place such as a doctor room or stored in a recording unit such as an optical disk, and can also be diagnosed by a doctor in the remote place. The information can also be recorded on a film 6110 serving as a recording medium by a film processor 6100 serving as a recording unit.

The exemplary embodiments of the present invention can also be implemented when a computer or a control computer executes a program (computer program). A means for feeding a program to the computer, e.g., a computer readable recording medium such as a compact disk read only memory (CD-ROM) that has recorded the program or a transmission medium such as the Internet that transmits the program can also be applied as an exemplary embodiment of the present invention. The above described program is also applicable as an exemplary embodiment of the present invention. The above described program, recording medium, and transmission medium, and a program product are included in a category of the present invention.

While the present invention has been specifically described above based on the exemplary embodiments, the present invention is not limited to the specific exemplary embodiments. Various forms are also included in the category of the present invention without departing from the scope of the present invention. Further, each of the above described exemplary embodiments only illustrates an exemplary embodiment of the present invention, and the exemplary embodiments can also be combined, as needed.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-080435, filed Apr. 9, 2015, which is hereby incorporated by reference herein in its entirety.

What is claimed is:

1. A radiation imaging apparatus comprising:
   an imaging pixel configured to acquire a radiation image, wherein the imaging pixel includes an imaging switching element for outputting a signal from an imaging conversion element;
   a detection pixel configured to detect radiation incidence, wherein the detection pixel includes a detection switching element for outputting a signal from a detection conversion element;
   a first control line electrically connected to a control electrode of the imaging switching element;
   a second control line electrically connected to a control electrode of the detection switching element;
   a signal line electrically connected to a main electrode of the detection switching element;
   a capacitance line arranged to be capacitively coupled with the signal line, wherein the capacitance line is different from the first control line and the second control line;
   a driving unit electrically connected to the second control line and the capacitance line and configured to apply a voltage to the detection switching element and the capacitance line; and
   a control unit configured to control the driving unit to apply, in a case where an on-state or off-state voltage is applied to the detection switching element, a voltage having an opposite polarity to that of the on-state or off-state voltage to the capacitance line.

2. The radiation imaging apparatus according to claim 1, wherein the control unit controls the driving unit so that a timing at which the on-state or off-state voltage is applied and a timing at which the voltage having the opposite polarity is applied overlap each other.

3. The radiation imaging apparatus according to claim 1, wherein the control unit controls the driving unit so that a timing at which the on-state or off-state voltage is applied coincides with a timing at which the voltage having the opposite polarity is applied.

4. The radiation imaging apparatus according to claim 1, wherein $\frac{1}{2} \times Cp \times Vpp < Cc \times \Delta Vc < 2 \times Cp \times Vpp$, is satisfied; and
   wherein Cgs is a capacitance formed between the second control line and the signal line, $\Delta Vpp$ is a voltage difference applied to the second control line, Cc is a capacitance of a capacitively coupled portion, and $\Delta Vc$ is a voltage difference applied to the capacitance line.

5. The radiation imaging apparatus according to claim 1, wherein the capacitance line is arranged side by side in the same direction with respect to the control line.

6. The radiation imaging apparatus according to claim 1, wherein the capacitance line is arranged so as to overlap the signal line.

7. The radiation imaging apparatus according to claim 1, wherein the capacitively coupled portion is arranged outside an imaging region in which the imaging pixel is arranged.

8. The radiation imaging apparatus according to claim 1, wherein the capacitively coupled portion is formed in a region overlapping the imaging pixel and/or the detection pixel.

9. The radiation imaging apparatus according to claim 1,
   wherein the detection switching element includes a thin film transistor, and
   wherein the capacitively coupled portion includes a switching element having the same structure as that of the thin film transistor.

10. The radiation imaging apparatus according to claim 1, wherein the detection pixel further includes an imaging conversion element and an imaging switching element connected to the imaging conversion element.

11. A radiation imaging system comprising:
    a radiation source configured to generate radiation; and
    the radiation imaging apparatus according to claim 1.

12. A radiation imaging apparatus comprising:
    an imaging pixel configured to acquire a radiation image, wherein the imaging pixel includes an imaging switching element for outputting a signal from an imaging conversion element;
    a detection pixel configured to detect radiation incidence, wherein the detection pixel includes a detection switching element for outputting a signal from a detection conversion element;
    a driving unit configured to apply a voltage for controlling an output through the imaging switching element to the imaging switching element via a first control line, and to apply a voltage for controlling an output through the detection switching element to the detection switching element via a second control line;
    a signal line for transmitting a signal output through the detection switching element;
    a capacitance line arranged to be capacitively coupled with the signal line, wherein the capacitance line is different from the first control line and the second control line; and
    a control unit configured to perform control to change, in a case where the driving unit changes a voltage applied to the detection switching element via the second control line, a voltage applied to the capacitance line to have an opposite polarity to that of the changed voltage to suppress a variation of a signal transmitted to the signal line caused by a charge generated on the signal line via a parasitic capacitance between the second control line and the signal line.

13. A radiation imaging system comprising:
    a radiation source configured to generate radiation; and
    the radiation imaging apparatus according to claim 12.

14. A radiation imaging apparatus comprising:
    an imaging pixel configured to acquire a radiation image, wherein the imaging pixel includes an imaging switching element for outputting a signal from an imaging conversion element;
    a detection pixel configured to detect radiation incidence, wherein the detection pixel includes a detection switching element for outputting a signal from a detection conversion element;
    a driving unit configured to apply a voltage for controlling an output through the imaging switching element to the imaging switching element via a first control line, and to apply a voltage for controlling an output through the detection switching element to the detection switching element via a second control line;

a signal line for transmitting a signal output through the detection switching element;

a capacitance line arranged to be capacitively coupled with the signal line, wherein the capacitance line is different from the first control line and the second control line; and a control unit configured to perform control to change, in a case where the driving unit changes a voltage applied to the detection switching element via the second control line, a voltage applied to the capacitance line to suppress a variation of a signal transmitted to the signal line caused by a charge generated on the signal line via a parasitic capacitance between the second control line and the signal line.

15. A radiation imaging system comprising:
a radiation source configured to generate radiation; and
the radiation imaging apparatus according to claim 14.

* * * * *